(12) United States Patent
Masserini et al.

(10) Patent No.: US 10,010,505 B2
(45) Date of Patent: *Jul. 3, 2018

(54) LIPOSOMES ACTIVE IN-VIVO ON NEURODEGENERATIVE DISEASES

(71) Applicant: UNIVERSITA DEGLI STUDI DI MILANO-BICOCCA, Milan (IT)

(72) Inventors: Massimo Masserini, Santa Margherita Ligure (IT); Francesca Re, Busto Garolfo (IT); Giulio Sancini, Gessate (IT); Gianluigi Forloni, Rho (IT); Mario Salmona, Milan (IT)

(73) Assignee: UNIVERSITA DEGLI STUDI DI MILANO-BICOCCA, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/505,481

(22) Filed: Oct. 2, 2014

(65) Prior Publication Data

US 2015/0017235 A1    Jan. 15, 2015

Related U.S. Application Data

(63) Continuation of application No. 13/536,851, filed on Jun. 28, 2012, now Pat. No. 8,877,236.

(51) Int. Cl.
*A61K 9/127* (2006.01)
*A61K 9/00* (2006.01)
*A61K 47/48* (2006.01)

(52) U.S. Cl.
CPC .......... *A61K 9/1275* (2013.01); *A61K 9/0019* (2013.01); *A61K 9/1277* (2013.01); *A61K 47/48246* (2013.01)

(58) Field of Classification Search
CPC .................................................. A61K 9/1275
See application file for complete search history.

(56) References Cited

U.S. PATENT DOCUMENTS 8,877,236 B2 * 11/2014 Masserini et al. ............. 424/450
2004/0204354 A1 * 10/2004 Nelson et al. .................. 514/12

FOREIGN PATENT DOCUMENTS

WO    WO 2009150686 A1 * 12/2009

OTHER PUBLICATIONS

Re et al, "Functionalization of liposomes with ApoE-derived peptides at different density affects cellular uptake and drug transport across a blood-brain barrier model," Nanomedicine: Nanotechnology, Biology, and Medicine, vol. 7, Issue 5, pp. 551-559 (May 20, 2011).*
Goedert et al, "A Century of Alzheimer's Disease," Science, vol. 314, No. 5800, pp. 777-781 (2006).*
Holmes et al, "Long-Term Effects of Aβ42 Immunisation in Alzheimer's Disease: Follow-Up of a Randomised, Placebo-Controlled Phase I Trial," The Lancet, vol. 372, Issue 9634, pp. 216-223 (2008).*
Pahnke et al, "Alzheimer's Disease and Blood—Brain Barrier Function—Why Have Anti-β-Amyloid Therapies Failed to Prevent Dementia Progression?", Neuroscience and Biobehavioral Reviews, vol. 33, Issue 7, pp. 1099-1108 (2009).*

* cited by examiner

*Primary Examiner* — Dennis J Parad
(74) *Attorney, Agent, or Firm* — Steinfl + Bruno LLP

(57) ABSTRACT

New liposomes are described, comprising: (i) phosphatidic acid and/or cardiolipin; (ii) apolipoprotein E (ApoE) or derivatives thereof. The so modified liposomes, administered systemically, obtain a dramatic in-vivo reduction of the amyloid plaque in the central nervous system, allowing an effective treatment of neurodegenerative diseases, in particular Alzheimer's disease.

16 Claims, 2 Drawing Sheets

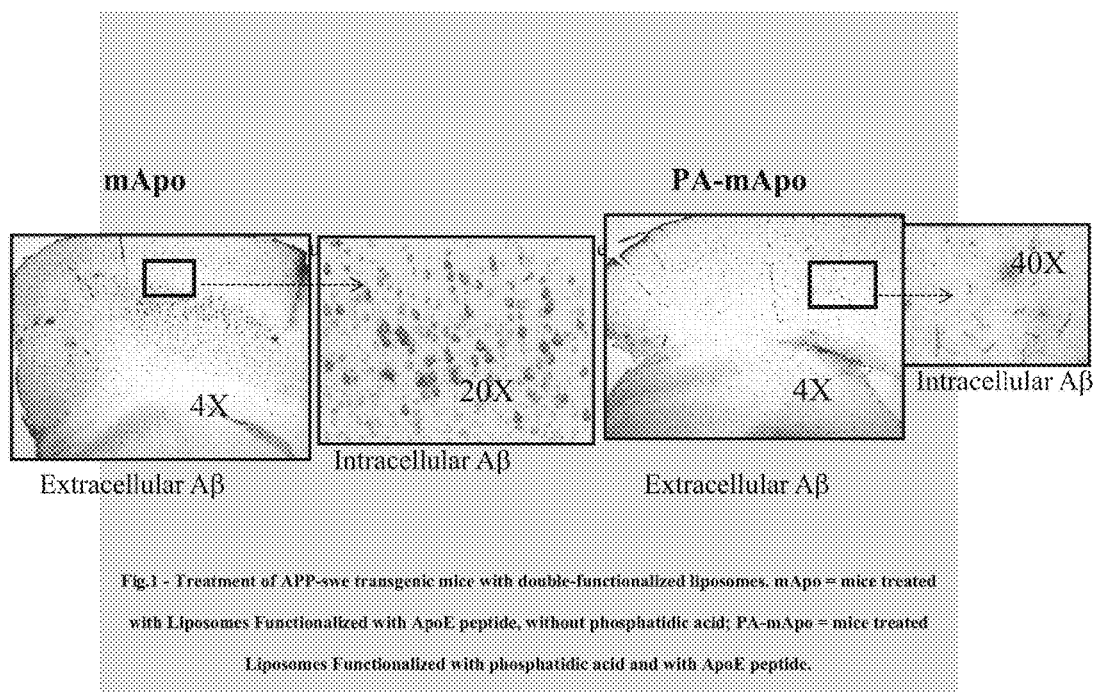
Fig.1 - Treatment of APP-swe transgenic mice with double-functionalized liposomes. mApo = mice treated with Liposomes Functionalized with ApoE peptide, without phosphatidic acid; PA-mApo = mice treated Liposomes Functionalized with phosphatidic acid and with ApoE peptide.

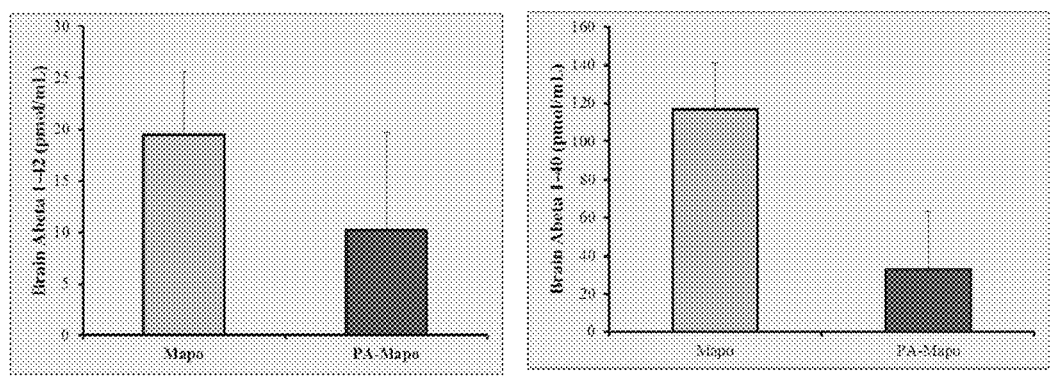
*Figure 2. Content of Aβ 40 or 42 in brain homogenates of animals treated with liposomes functionalized with ApoE (mApo) or ApoE + phosphatidic acid (PA-mApo).*

LIPOSOMES ACTIVE IN-VIVO ON NEURODEGENERATIVE DISEASES

CROSS REFERENCE TO RELATED APPLICATIONS

The present application is a continuation of U.S. patent application Ser. No. 13/536,851 entitled "Liposomes active in vivo on neurodegenerative diseases" filed Jun. 28, 2012, the entire disclosure of which is incorporated herein by reference.

FIELD

The present disclosure relates to liposomes and in particular to modified liposomes and related compositions methods and systems.

BACKGROUND

Alzheimer's disease is a neurodegenerative disease characterized by progressive loss of memory and cognitive function. It is classifiable as dementia and it is likely to be the fourth most common cause of death in industrialized countries, in addition to causing incalculable social and economic harm. The post-mortem observation of brain tissues of Alzheimer's patients reveals the presence of senile plaques and neurofibrillary tangles in the limbic system and cortex. The plaques, which are mainly present in the extra-cellular level, contain as a major component the β-amyloid peptide with 40 or 42 amino acids; the β-amyloid peptide (herein abbreviated Aβ) is produced in significant amounts in the brain of patients in the form of monomer, and tends to associate to form increasingly larger aggregates (oligomers, fibrils, plaques). These aggregates are toxic to neurons, leading to their degeneration responsible for progressive loss of cognitive ability and ultimately death. The peptide Aβ, produced in abnormally high amounts in Alzheimer's disease, accumulates in the brain. The dynamic equilibrium between different aggregation forms justifies the fact that the increased production of monomers in the disease, is shifting the equilibrium towards the formation of plaques. The Aβ peptide is also found in the bloodstream where it is possibly in equilibrium, through the blood-brain barrier, with the one present in the brain. As an evidence of the existence of this equilibrium, papers by other authors have shown that the administration of substances capable to bind the peptide Aβ in the blood and to remove it, can to some extent indirectly promote the efflux of Aβ from the CNS: this effects is generally known as "sink effect".

Whenever successful however, the sink effect has so far obtained a modest, unsatisfactory reduction of the plaque. For example, the literature reports a reduction of the amyloid plaque by using anti-Aβ antibodies or gangliosides; however these substances, beyond providing a modest plaque reduction, are associated with risks of serious side effects on the immune system, e.g. meningoencephalitis (J. Neurosci. 2011, 31(25), 9323-31). The patent application WO 2009/150686 describes liposomes based on cholesterol and sphingomyelin, and a further lipid chosen from cardiolipin, phosphatidic acid and phosphatidylglycerol; these products have a binding capacity with the Aβ peptide in-vitro.

Although some examples of Aβ peptide binding substances are known, at present there is no evidence that any such substances can bring about a therapeutically significant reduction of the amyloid plaque in the brain after systemic administration. The need is therefore felt for treatments being strongly effective against the amyloid plaque in-vivo, so as to represent a valid treatment of Alzheimer's diseases and other neurodegenerative conditions.

SUMMARY

The present invention concerns new liposomes comprising: (i) phosphatidic acid and/or cardiolipin; (ii) apolipoprotein E (ApoE) or derivatives thereof, additionally to standard liposome lipids. The so modified liposomes, administered systemically, obtain a dramatic in-vivo reduction of the amyloid plaque. This invention represents the first example of a strong therapeutic response to Aβ peptide binding strategies, which is obtained in-vivo at moderate doses, using agents having low toxicity risks, allowing an effective treatment of neurodegenerative diseases, in particular Alzheimer's disease. A further embodiment of the invention is a process to prepare the said liposomes comprising mixing the above described components (i) and (ii) with standard liposome lipids, for a time and under conditions suitable to provide a liposome. A further embodiment is a pharmaceutical composition comprising the above described liposomes and one or more pharmaceutically acceptable excipients. A further embodiment is a method for treating or preventing a neurodegenerative disease of the central nervous system, comprising administering to an individual in need thereof, an effective amount of said liposomes. A further embodiment is a method for in-vivo preventing, reducing or eliminating the amyloid plaque in the central nervous system of an individual, comprising administering to said individual an effective amount of the above described liposomes.

BRIEF DESCRIPTION OF THE DRAWINGS

FIG. 1: Treatment of APP-swe transgenic mice with double-functionalized liposomes. mApo=mice treated with Liposomes Functionalized with ApoE peptide, without phosphatidic acid; PA-mApo=mice treated with Liposomes Functionalized with phosphatidic acid and with ApoE peptide.

FIG. 2: Content of Aβ 40 or 42 in brain homogenates of APP-swe transgenic mice treated with liposomes functionalized with ApoE (mApo) or ApoE+phosphatidic acid (PA-mApo).

DETAILED DESCRIPTION

The term "liposome" as described herein indicates a vesicle composed of a lipid bilayer comprising amphiphilc lipids typically having a hydrophobic hydrocarbon tail and apolar hydrophilic head. Exemplary liposomes comprise multilamellar vesicle (MLV), small unilamellar vesicle (SUV), and large unilamellar vesicle (LUV), readily identifiable by a skilled person.

The term "phosphatidic acid" used herein means a molecule having a glycerol backbone esterified with two fatty acids and one phosphate group, for example dimiristoyl-phosphatidic acid. Cardiolipin is a well-known compound, also known as 1,3-bis(sn-3'-phosphatidyl)-sn-glycerol. In the liposome, the phosphatidic acid (or cardiolipin) is preferably present in the following approximate molar amounts (with respect to the total moles of all substances making up the liposome): 1-20%, more preferably 1-10%, most preferably 5% molar amount. If phosphatidic acid or cardiolipin are both present, the above ranges are referred to the sum of moles of both substances; when both present, phosphatidic acid and cardiolipin can be used in any mutual ratio.

Apolipoprotein E (herein also referred as ApoE) is a 34 kDa glycoprotein containing 299 aminoacids, produced in high levels in liver and brain. ApoE can be used as obtained from its natural sources or be synthetized on purpose. The term "ApoE derivatives" includes the known ApoE isoforms, coded E2, E3. The term "ApoE derivative" also includes fragments of ApoE, preferably those comprised within the portion from amino acid residue 100 to amino acid residue 200 of ApoE amino acid sequence; a specific preferred fragment is the sequence from amino acid residue 141 to amino acid residue 150 of ApoE (Sequence: (LRKLRKRLLR)-NH$_2$), or dimer thereof (Sequence: (LRKLRKRLLR)-(LRKLRKRLLR)-NH$_2$). Preferably, the ApoE or derivative thereof includes, at the C-terminal end, a cystein-ending small peptide (up to five aminoacids), more preferably a tripeptide, most preferably the tripeptide CWG-; such small peptide assists in the chemical linkage to the lipid: preferred examples of the resulting fragments are: CWG-(LRKLRKRLLR)-NH$_2$, herein "mApoE", or CWG-(LRKLRKRLLR)-(LRKLRKRLLR)-NH$_2$, herein "dApoE".

The ApoE may be present in the liposomes as a physical mixture with the other lipids constituents of the liposome membrane, be deposited on such membrane, be chemically linked to these lipids, be contained within the liposome, be added to existing liposomes, or be comprised in any additional configuration to include said ApoE in the liposome which will be identifiable by a skilled person. Preferably, ApoE is chemically linked. In this case, the ApoE as above described may be linked or connected via a linker molecule; a preferred linker is the compound 1,2 stearoyl-sn-glycero-3-phosphoethanolamine-N-[maleimide(poly(ethylene glycol)-2000)] (herein abbreviated "mal-PEG-PE"). In the final liposome, the ApoE is preferably present in a molar amount of 1-5% (with respect to the total moles of all substances making up the liposome).

The final liposome further comprises standard liposome lipids; the term "standard liposome lipids" indicates lipids that are usually included in liposomes that are identifiable by the skilled person. These make up the bulk of the liposome, preferably accounting for a 90-98% molar amount (with respect to the total moles of all substances making up the liposome). Preferred standard liposome lipids are sphingomyelin, phosphatidylcholine, phosphatidylethanolamine (PEGylated or not) and cholesterol.

The above described liposomes are per se fully effective on the amyloid plaque in-vivo, as herein demonstrated; as an option, they may additionally include further active agents, also useful for the intended treatment; in such case the present liposomes perform the double function of drug and drug carrier.

A further embodiment on the invention is a process to prepare the above described liposomes. The liposome preparation process can be any known method to prepare liposomes comprising mixing the above described components (i), (ii), with the above described standard liposome lipids, for a time and under conditions suitable to provide a liposome.

Examples of known methods to prepare liposomes are: extrusion, lipid hydration, solvent spherule method, sonication, French press cell, solvent injection, detergent removal, reserve phase evaporation, calcium-induced fusion, microfluidization, freeze-thawing, freeze-drying, etc. The ApoE-adding step, typical of the present invention, is performed in function of the desired mode of connection with ApoE. For example, if ApoE is added as a physical mixture with the other lipids, a suitable procedure may involve:

(a) mixing in a solvent: the components (i) and standard liposome lipids;
(b) drying the mixture of step (a);
(c) rehydrating the mixture of step (b) in a buffer solution;
(d) stirring and then extruding the solution of step (c) through a filter with suitable pore size, e.g. 100 nm;
(e) adding component (ii);

If ApoE is added via a linker molecule, a suitable procedure may involve:

(a) mixing in a solvent: the components (i), the linker molecule and standard liposome lipids
(b) drying the mixture of step (a);
(c) rehydrating the mixture of step (b) in a buffer solution;
(d) stirring and then extruding the solution of step (c) through a filter having suitable pore size, e.g. 100 nm;
(e) purifying the filtered solution of step (d);
(f) resuspending in a buffer the purified solution of step (e) and mixing it with the component (ii);
(g) purifying the solution of step (f), and final drying.

Additional procedures and techniques to provide the liposomes herein described can be identified by a skilled person upon reading of the present disclosure.

A further embodiment of the invention is a pharmaceutical composition comprising the above described liposomes, together with one or more pharmaceutically acceptable excipients and, optionally, further active agents.

The term "excipient" as used herein indicates an inactive substance used as a carrier for the active ingredients of a medication. Suitable excipients for the pharmaceutical compositions herein disclosed include any substance that enhances the ability of the body of an individual to absorb a liposome herein described. Suitable excipients also include any substance that can be used to bulk up formulations with a modified liposome herein described, to allow for convenient and accurate dosage. In addition to their use in the single-dosage quantity, excipients can be used in the manufacturing process to aid in the handling of a liposome herein described. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents. The term "excipient" used herein also extends to vehicles and/or diluents, wherein: "vehicles" indicates any of various media acting usually as solvents or carriers; "diluent" indicates a diluting agent which is issued to dilute an active ingredient of a composition; suitable diluent include any substance that can decrease the viscosity of a medicinal preparation.

The type and amounts of excipients are chosen in function of the chosen pharmaceutical form; suitable pharmaceutical forms are liquid systems like solutions, infusions, suspensions; semisolid systems like colloids, gels, pastes or cremes; solid systems like powders, granulates, tablets, capsules, pellets, microgranulates, minitablets, microcapsules, micropellets, suppositories; etc. Each of the above systems can be suitably be formulated for normal, delayed or accelerated release, using techniques well-known in the art.

A further embodiment of the invention is the use of the above described liposomes or pharmaceutical compositions in a method to treat or prevent neurodegenerative diseases of the central nervous system, in particular Alzheimer's diseases and other forms of dementia. The invention further extends to the above liposomes or pharmaceutical compositions for use in therapy. The invention further comprises the above liposomes or pharmaceutical compositions for use in treating or preventing neurodegenerative diseases of the central nervous system, in particular Alzheimer's diseases and other forms of dementia. The invention also comprises the use of the above liposomes or pharmaceutical compositions in the manufacturing of a medicament for treating or preventing neurodegenerative diseases of the central nervous system, in particular Alzheimer's diseases and other forms of dementia.

The liposome are especially active in inhibiting (i.e. preventing, reducing or eliminating; eliminating being preferred) in-vivo the amyloid plaque in the central nervous system of patients suffering from or being at risk of developing the above diseases; as an additional advantage, said plaque inhibition takes place in the CNS both at extracellular and intracellular level, thus extending the activity to all Aβ deposits present in the central nervous system: this is an essential prerequisite to achieve a total elimination of the plaque.

The invention thus includes therapeutic methods and medical uses aimed at inhibiting in-vivo the amyloid plaque in the central nervous system of an individual suffering from or being at risk of developing the above diseases, characterized by the administration of the above described liposomes or pharmaceutical compositions.

The invention further includes the use of the modified liposome or compositions and in particular pharmaceutical compositions herein described in a method to treat or prevent a condition associated to presence of amyloid plaque in an individual.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof. The wording "associated to" as used herein with reference to two items indicates a relation between the two items such that the occurrence of a first item is accompanied by the occurrence of the second item, which includes but is not limited to a cause-effect relation and sign/symptoms-disease relation. The term "individual" as used herein includes a single biological organism wherein amyloid peptide can occur including but not limited to animals and in particular higher animals and in particular vertebrates such as mammals and in particular human beings.

The above treatments can be performed by delivering the above liposomes/pharmaceutical compositions to an individual in need thereof, in suitable dose unit, via any suitable administration route.

Suitable dose units are comprised in the 1-15 mmoles total lipids for an average 70 kg person. All administration routes (enteral, parenteral) enabling a systemic distribution of the medicament are contemplated. Example of possible administration routes are: oral, intravenous, intramuscular, inhalatory, intratracheal, intraperitoneal, buccal, sublingual, nasal, subcutaneous, transdermal, transmucosal. Preferred is the inhalatory or intratracheal route. In the present invention, the administration routes directly into the central nervous system (i.e. into those areas placed beyond the blood brain barrier) are definitely not necessary for the present liposomes, since they are advantageously active in the CNS via simple systemic administration. From the therapeutic perspective it is primarily important that the treatment with the present liposomes obtains a strong in-vivo reduction of the amyloid plaque via systemic administration, by means of a low-toxicity active agent, exempt from side effects, at moderate dosages. A long-wanted in-vivo effective treatment is thus provided, easy-to-perform, involving a non-expensive process of preparation, useful for the treatment and prevention of diseases depending from the formation of amyloid plaque, in particular neurodegeneration in the central nervous system, more particularly Alzheimer's diseases and related dementias.

Further characteristics of the present disclosure will become more apparent hereinafter from the following detailed disclosure by way or illustration only with reference to an experimental section.

EXAMPLES

The modified liposomes, compositions methods and system herein described are further illustrated in the following examples, which are provided by way of illustration and are not intended to be limiting. A person skilled in the art will appreciate that modified liposomes indicated in the examples, are only one exemplary of modified liposomes and that modified liposomes can include additional modified liposomes in accordance with the present disclosure as well as related compositions methods and systems.

1. Preparation of Liposomes
Liposomes composition:
5 mol % phosphatidic acid
2.5 mol % PEG-PE-maleimide (mal-PEG-PE) assisting in the chemical linkage to the ApoE:
46.25 mol % cholesterol
46.25 mol % sphingomyelin The liposomes were prepared by extrusion technique. The lipids were mixed in an organic solvent (chloroform/methanol 2:1, v:v), which was subsequently removed by a gentle flow of nitrogen, followed by vacuum pump for at least 3 hours. The so obtained lipid film was resuspended in physiological buffer (150 mM NaCl, pH 7.40) and extruded 10 times under pressure (20 bar) at a temperature of 55° C. through polycarbonate filters with pore diameter of 100 nm using an Extruder (Lipex Biomembranes).

The mApoE peptide was added to the liposomes in the molar ratio of 1.2:1 (peptide: mal-PEG-PE) and the mixture was incubated overnight at room temperature. The next day the mixture was injected intratracheally (i.t.) into healthy mice (for pharmacokinetic tests) or in transgenic mice for Alzheimer's disease (for tests on amyloid plaque)

2. Animal Models
Balb/C healthy mice
C56 mice transgenic for the mutant APP-swe.
C56 mice transgenic for the APP-PS1 double mutation 3. Pharmacokinetic Tests
A group of healthy mice received i.t. administered liposomes containing phosphatidic acid and mApoE and comprising radioactive (3H-SM) sphingomyelin, following this treatment schedule: 1 injection every 2 days for 5 days of 100 uL aliquot (40 mM total lipid) of a liposomes. The animals were sacrificed at various times after administration. The organs were taken and processed for measuring radioactivity through liquid scintillation.

The results reported below refer to the measurements of radioactivity in the brain, reported as % of total close administered.

The radioactivity in the brain after the 3$^{rd}$ administration indicated a presence of 0.7% of the administered dose, corresponding to substantially very low amount reaching the brain.

4. Tests On Amyloid Plaque In-Vivo

A first group of APP-swe mice (genetically modified for Alzheimer's disease) was administered with liposomes containing phosphatidic acid, and mApoE (group "PA-Mapo", n=6), a second group of mice APP-swe received the same liposomes but without phosphatidic acid (Group "Mapo", n=6). In both cases, the treatment consisted of 3 i.t. injections per week for 3 weeks, 1.00 µL of a 40 mM liposome suspension per injection. The mice were finally sacrificed and the brain removed. Cryo-sections were prepared for subsequent histological examination and homogenates for ELISA. The histological analysis was performed on cryo-sections of the brain using anti-Aβ antibodies and subsequent staining with secondary antibodies HRP/chromogen. Staining (brown) corresponds to Aβ deposits.

Histological Examination Results

As can be seen in FIG. 1 (images before and after treatment in the group "PA-Mapo"), the treatment with the liposomes of the invention has removed the deposits of Aβ; removal was found effective at both extra and intra-cellular level. In particular, the total elimination of deposits was observed in 4 out of 6 treated animals. Conversely in the "Mapo" group, no removal of Aβ deposits was observed.

This confirms the efficacy of the method in accordance with the invention. In particular it can be deduced that only the association ApoE+PA allows to obtain the vivo reduction/elimination of Aβ peptide deposits.

ELISA Results

After extraction with formic acid from brain tissue, the total content of beta-amyloid (1-40 and 1-42) was quantified by ELISA assay. As can be seen from FIG. 2, it is noted a significant decrease of the total content of the two forms of Aβ in the PA-Mapo group, compared to the mApo group.

The examples set forth above are provided to give those of ordinary skill in the art a complete disclosure and description of how to make and use the embodiments of modified liposomes and related compositions methods and systems of the disclosure, and are not intended to limit the scope of what the inventors regard as their disclosure. Modifications of the above-described modes for carrying out the disclosure can be used by persons of skill in the art, and are intended to be within the scope of the following claims.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

The invention claimed is:

1. Liposomes consisting of:
   (i) phosphatidic acid and/or cardiolipin in a 1-10% molar amount,
   (ii) apolipoprotein E or derivatives thereof in a 1-5% molar amount, and
   (iii) standard liposome lipids,
      wherein said apolipoprotein E or derivative thereof is linked to a compound 1,2 stearoyl-sn-glycero-3-phosphoethanolamine-N-[maleimide(poly(ethylene glycol)-2000)].

2. Liposomes according to claim 1, wherein the component (ii) is an apolipoprotein E fragment comprised within the portion from amino acid residue 100 to amino acid residue 200 of Apolipoprotein E amino acid sequence.

3. Liposomes according to claim 1, wherein the component (ii) corresponds to the sequence from amino acid residue 141 to amino acid residue 150 of apolipoprotein E, or a dimer thereof.

4. Liposomes according to claim 1, wherein said apolipoprotein E or derivative thereof has a C-terminal end and includes, at said C-terminal end, a cysteine-ending peptide of up to five amino acids.

5. Liposomes according to claim 4, wherein the cysteine-ending peptide is the tripeptide CWG.

6. Liposomes according to claim 1, wherein the standard liposomes lipids are selected from the group consisting of one or more among sphingomyelin, phosphatidylcholine, phosphatidylethanolamine, PEGylated phosphatidylethanolamine, and cholesterol.

7. Liposomes according to claim 1, wherein the standard liposomes lipids are cholesterol and sphingomyelin, in substantially equimolar ratio.

8. Liposomes according to claim 1, wherein the component (i) is present in an approximate 5% molar percentage.

9. Pharmaceutical composition comprising the liposomes of claim 1 and one or more pharmaceutically acceptable excipients.

10. Pharmaceutical composition according to claim 9, formulated for a systemic administration route.

11. A method for treating a neurodegenerative disease of the central nervous system, comprising administering to an individual in need thereof, an effective amount of the liposomes of claim 1.

12. The method according to claim 11, wherein the disease is Alzheimer's disease or other dementias.

13. A method for in-vivo reducing or eliminating the amyloid plaque in the central nervous system of an individual, comprising administering to said individual an effective amount of the liposomes of claim 1.

14. The method of claim 13, wherein said administered amount of liposomes is effective in reducing or eliminating the amyloid plaque at both intracellular and extracellular level.

15. The method of claim 13, wherein the individual suffers from or is at risk to develop a neurodegenerative disease of the central nervous system.

16. A process to prepare the liposomes of claim 1 comprising:
 (a) mixing in a solvent: the components (i), the compound 1,2 stearoyl-sn-glycero-3-phosphoethanolamine-N-[maleimide(poly(ethylene glycol)-2000)] and the standard liposome lipids (iii);
 (b) drying the mixture of step (a);
 (c) rehydrating the mixture of step (b) in a buffer solution;
 (d) stirring and then extruding the solution of step (c) through a filter having a suitable pore size;
 (e) purifying the filtered solution of step (d);
 (f) resuspending in a buffer the purified solution of step (e) and mixing it with the component (ii); and
 (g) purifying the solution of step (f).

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: synthetic peptide

<400> SEQUENCE: 1

Leu Arg Lys Leu Arg Lys Arg Leu Leu Arg
1               5                   10

<210> SEQ ID NO 2
<211> LENGTH: 20
<212> TYPE: PRT
<213> ORGANISM: Artificial Sequence
<220> FEATURE:
<223> OTHER INFORMATION: synthetic peptide

<400> SEQUENCE: 2

Leu Arg Lys Leu Arg Lys Arg Leu Leu Arg Leu Arg Lys Leu Arg Lys
1               5                   10                  15

Arg Leu Leu Arg
            20

<210> SEQ ID NO 3
<211> LENGTH: 13
<212> TYPE: PRT
<213> ORGANISM: Artificial Sequence
<220> FEATURE:
<223> OTHER INFORMATION: synthetic peptide

<400> SEQUENCE: 3

Cys Trp Gly Leu Arg Lys Leu Arg Lys Arg Leu Leu Arg
1               5                   10

<210> SEQ ID NO 4
<211> LENGTH: 23
<212> TYPE: PRT
<213> ORGANISM: Artificial Sequence
<220> FEATURE:
<223> OTHER INFORMATION: synthetic peptide

<400> SEQUENCE: 4

Cys Trp Gly Leu Arg Lys Leu Arg Lys Arg Leu Leu Arg Leu Arg Lys
1               5                   10                  15

Leu Arg Lys Arg Leu Leu Arg
            20